United States Patent
Grodzki

(10) Patent No.: US 9,575,151 B2
(45) Date of Patent: Feb. 21, 2017

(54) MAGNETIC RESONANCE APPARATUS AND OPERATING METHOD

(71) Applicant: David Grodzki, Erlangen (DE)

(72) Inventor: David Grodzki, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 721 days.

(21) Appl. No.: 14/039,238

(22) Filed: Sep. 27, 2013

(65) Prior Publication Data

US 2014/0091794 A1   Apr. 3, 2014

(30) Foreign Application Priority Data

Sep. 28, 2012 (DE) ................. 10 2012 217 770

(51) Int. Cl.
*G01R 33/48* (2006.01)
*A61B 5/055* (2006.01)

(52) U.S. Cl.
CPC .......... *G01R 33/4816* (2013.01); *A61B 5/055* (2013.01); *G01R 33/4824* (2013.01)

(58) Field of Classification Search
CPC ........... G01R 33/4816; G01R 33/4824; G01R 33/482; A61B 5/055
See application file for complete search history.

(56) References Cited

U.S. PATENT DOCUMENTS

| 2005/0077895 A1 | 4/2005 | Hargreaves et al. |
| 2012/0074938 A1 | 3/2012 | Grodzki et al. |
| 2012/0235680 A1* | 9/2012 | Blumhagen .......... G01R 33/481 324/307 |
| 2013/0200893 A1 | 8/2013 | Heismann et al. |

OTHER PUBLICATIONS

Heid et al., "Rapid Single Point (RASP) Imaging," Institute of Diagnostic Radiology, University of Bern, Siemens Medical Engineering, 3rd Annual Meeting, (1995), p. 684.

(Continued)

*Primary Examiner* — Gregory H Curran
(74) *Attorney, Agent, or Firm* — Schiff Hardin LLP

(57) ABSTRACT

In a method to operate a magnetic resonance apparatus with a magnetic resonance sequence—in particular a PETRA sequence—in which k-space is radially scanned for an image acquisition in a first region of k-space that does not include the center of k-space, and in which an excitation pulse is radiated as the full strength of at least two phase coding gradients is reached, and in which k-space is scanned in a Cartesian manner—in particular by single point imaging—in a second region of k-space remaining without the first region, the gradient strength corresponding to a shortest total acquisition time is determined automatically from predetermined sequence parameters and/or sequence parameters defined by a user. The sequence parameters parameterize the magnetic resonance sequence and describe the number of acquisitions for the regions of k-space and the repetition time, and the gradient strength is indicated to a user as a recommendation and/or is set automatically in the implementation of the magnetic resonance sequence.

10 Claims, 2 Drawing Sheets

(56) References Cited

OTHER PUBLICATIONS

Nielles-Vallespin et al., "3D Radial Projection Technique With Ultrashort Echo Times for Sodium MRI: Clinical Applications in Human Brain and Skeletal Muscle," Magnetic Resonance in Medicine, vol. 57, (2007), pp. 74-81.

Grodzki et al., "Ultrashort Echo Time Imaging Using Pointwise Encoding Time Reduction With Radial Acquisition (PETRA)," Magnetic Resonance in Medicine, vol. 67, (2012), pp. 510-518.

Lee et al., "Time-Optimal Design for Multidimensional and Parallel Transmit Variable-Rate Selective Excitation," Magnetic Resonance in Medicine, vol. 61, (2009), pp. 1471-1479.

* cited by examiner

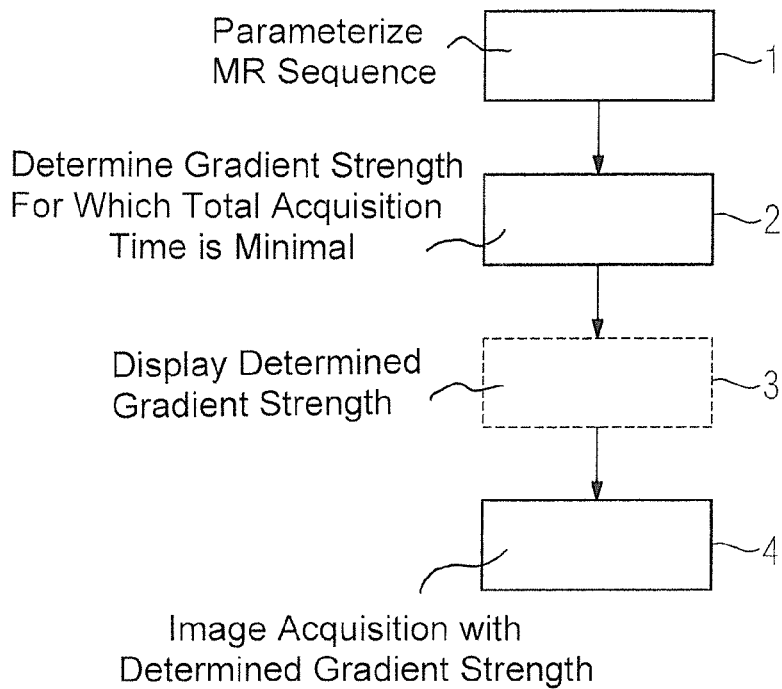
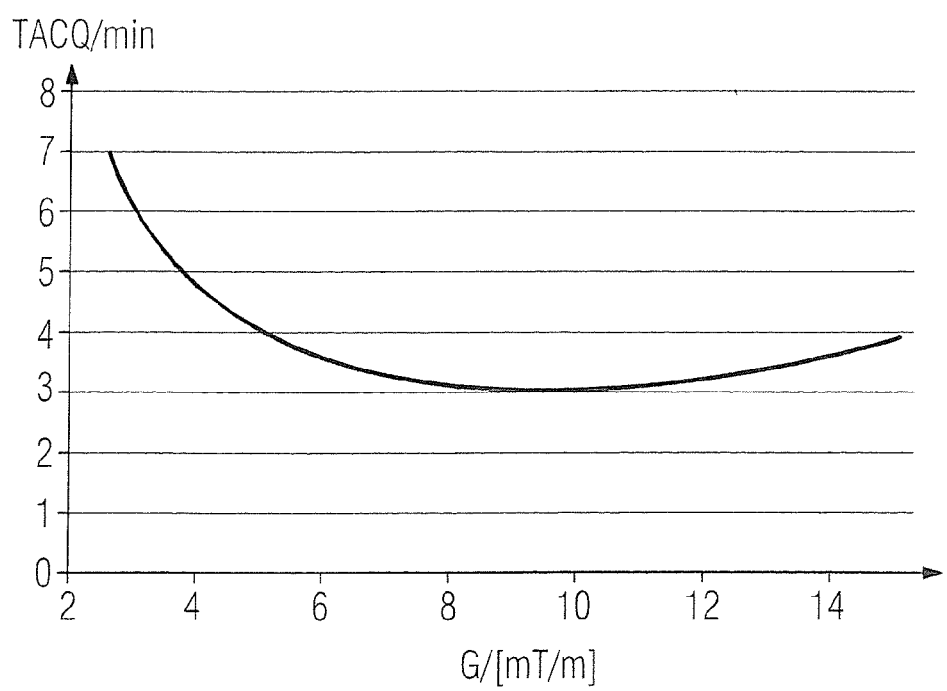

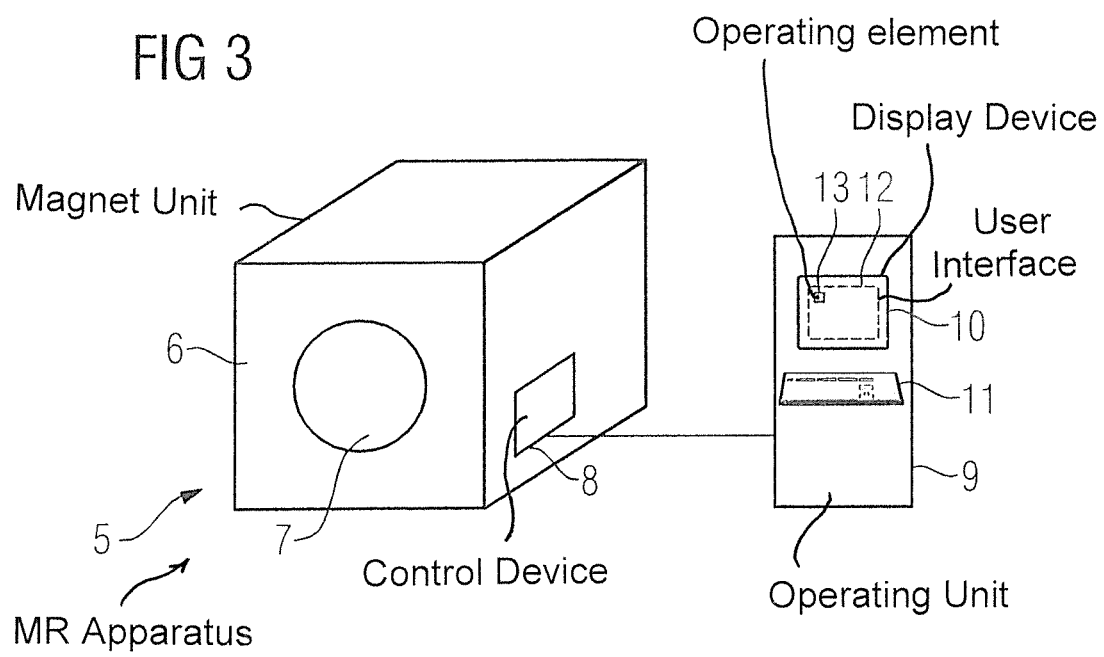

MAGNETIC RESONANCE APPARATUS AND OPERATING METHOD

BACKGROUND OF THE INVENTION

Field of the Invention

The present invention concerns: a method to operate a magnetic resonance device with a magnetic resonance sequence—in particular a PETRA (Pointwise Encoding Time Reduction with Radial Acquisition) sequence—radially scanned for an image acquisition in a first region of k-space that does not include the center of k-space, with an excitation pulse that is radiated as the full strength of the at least two phase coding gradients is reached, and in which k-space is scanned in a Cartesian manner—in particular by single point imaging—in a second, remaining region of k-space other than the first region. The invention concerns a magnetic resonance device implements such a method.

Description of the Prior Art

Magnetic resonance sequences in which extremely short ("ultrashort") echo times are used offer new fields of use in magnetic resonance imaging. Materials can be made visible with ultrashort echo times—for example bones, ligaments, tendons or teeth—that would not be measurable with conventional sequences (for example in echo sequences or gradient echo sequences) due to their rapidly decaying magnetic resonance signal. Fields of application are therefore, for example, orthopedics, dental or skeletal imaging, and magnetic resonance positron emission tomography attenuation correction.

In the prior art, various magnetic resonance sequences have been developed that have such ultrashort echo times, for example echo times TE<500 µs.

One example of such a magnetic resonance sequence is the radial UTE (ultrashort echo time) sequence, for example as described in an article by Sonia Nielles-Vallespin, "3D radial projection technique with ultrashort echo times for sodium MRI: clinical applications in human brain and skeletal muscle", Magn. Reson. Med. 2007; 57; Pages 74-81. After a wait time after a non-slice-selective or slice-selective excitation, the gradients are ramped up and begun simultaneously with the data acquisition, wherein the k-space trajectory scanned in such a manner proceeds radially outwardly from the k-space center after an excitation. Before the image data are determined by means of Fourier transformation from the raw data acquired in k-space, the latter must initially be converted into a Cartesian k-space grid (for example via regridding).

An additional known approach for ultrashort echo times <500 µs is to scan k-space in points in that the "free induction decay" (FID) is detected. Such methods are typically designated as single point imaging since essentially only one raw data point in k-space is detected per radio-frequency excitation. The RASP ("rapid single point imaging") method is an example for such a single point imaging, which is described in an article by O. Heid and M. Deimling, "Rapid Single Point (RASP) Imaging", SMR, 3rd annual meeting, Page 684, 1995, for example. At a fixed point in time after the radio-frequency excitation at the "echo time" TE, a raw data point in k-space is read out whose phase has been coded by gradients. The gradient strength, together with the echo time, consequently thereby determines the point that is read out. The gradients are changed by means of the magnetic resonance system for each raw data point or, respectively, measurement point, and k-space is thus scanned point by point.

The two presented variants—thus UTE sequences and single point imaging—both have disadvantages, in particular that the methods take a very long measurement time.

In this regard, a magnetic resonance sequence has been proposed that combines both approaches into a more time-effective method, known as the PETRA sequence ("Pointwise Encoding Time Reduction with Radial Acquisition"). The PETRA sequence is described in, for example, an article by David. M. Grodzki et al., "Ultrashort echo time imaging using pointwise encoding time reduction with radial acquisition (PETRA)", Magnetic Resonance in Medicine 67; Pages 510-518, 2012, and in DE 10 2010 041 446 A1, which is herewith incorporated by reference into the disclosure content of this Specification. In a PETRA magnetic resonance sequence, k-space corresponding to the imaging region is read out according to the following steps:

a) switching (activating) at least two phase coding gradients in a respective spatial direction by means of a gradient system of the magnetic resonance device, b) after the switched phase coding gradients have reached the full strength, radiating a non-slice-selective radio-frequency excitation pulse by means of a radio-frequency transmission/reception device of the magnetic resonance device, c) after a time t1 after the last radiated excitation pulse, acquiring echo signals by means of the radio-frequency transmission/reception device and entering these signals as raw data in k-space along a radial k-space trajectory predetermined by the strength of the phase coding gradients, d) repeating Steps a) through c) with different phase coding gradients until k-space corresponding to the imaging area is read out (filled) along radial k-space trajectories, in a first region depending on time t1, and e) reading out (filling) k-space corresponding to the imaging area that is not covered by the first region of k-space, and that includes at least the k-space center in a different manner than described by Steps a) through d).

One of the basic ideas of the PETRA sequence is to already switch the phase coding gradient fields before the excitation pulse and to wait until these gradient fields have reached their full strength, such that the echo time—thus the time that lies between the excitation via a radio-frequency excitation pulse and the start of the acquisition of the measurement data—can be reduced in the totality of k-space to be scanned radially in comparison to a UTE sequence. However, a region around the center of k-space cannot be read out in this way, such that it is proposed to read out this region in a Cartesian manner, in particular by means of a single point imaging method (for example RASP).

The sequence parameters describing the specific magnetic resonance sequence to be executed are thereby largely freely selected by the user. It is extremely complicated, however, to achieve short overall measurement times by an appropriately devised selection of parameters.

SUMMARY OF THE INVENTION

An object of the present invention is to provide an optimally short total acquisition time for various parameterizations of a magnetic resonance sequence that scans k-space both radially and in a Cartesian manner.

To achieve this object, in a method of the aforementioned type, according to the invention a gradient field strength corresponding to the shortest total acquisition time in the scanning of the first region is determined automatically from predetermined sequence parameters and/or sequence parameters defined by a user input that parameterize the magnetic resonance sequence and describe the number of acquisitions for the regions of k-space and the repetition time, and this gradient field strength is indicated to a user as a suggestion and/or is set automatically in the implementation of the magnetic resonance sequence.

The invention is based on the insight that, given a defined gradient strength used in the radial scanning of k-space, an optimum of the sum of the acquisition times results for the radial and Cartesian portion. The gradient strength for the scanning of radial trajectories in the second region of k-space ultimately determines how large the second region of k-space around the center of k-space (consequently the arising "hole") is. The higher the gradient strength in the radial scanning of k-space, the shorter the duration of the corresponding scanning processes. However, more individual points must therefore be scanned in a Cartesian manner.

An automated method is now made available that minimizes the measurement time, by selection of an optimal gradient strength in the radial scanning for the sequence parameters predetermined by the user and/or by the system. A correlation between the total acquisition time and the gradient strength is used for this purpose.

In other words, the phase coding gradients are already activated at their full gradient strength before application of the excitation pulse in the magnetic resonance sequence (which is in particular a PETRA sequence). The coding of the spins therefore already effectively starts as of the middle of the excitation pulse. Since the data acquisition cannot be begun directly after the excitation pulse for technical reasons (in particular reverberations and like), in the acquisition of radial spokes in k-space, the first measurement points near the center are missed and a spherical hole in k-space center arises, namely the second region. The greater the gradient strength, the faster the readout and the more measurement points that fall into this "hole".

The points situated in the second region are subsequently measured point-by-point in the Cartesian portion of the magnetic resonance sequence, with only one point being measured in each repetition, since phase disruptions can otherwise occur. The repetition times TR in the Cartesian portion and radial portion of the magnetic resonance sequence are also preferably kept the same in order to not disrupt or, respectively, contaminate the arising steady state.

If parameters describing the image readout—in particular the size of the field of view and the matrix size in k-space, the echo time, the number of radial spokes to be acquired in the first region of k-space and the time provided for the ramping of the phase coding gradients—are now used as sequence parameters in a concrete embodiment of the present invention, a correlation between the total acquisition time and the gradient strength can be derived analytically, which is briefly presented in the following.

The size (extent) of the field of view is thereby designated with FOV; the matrix size in k-space (describing the totality of measurement points to be determined and Cartesian measurement points derived from the radial measurements) is designated with N; the echo time is designated with TE; the number of radial spokes to be acquired is designated with $N_{rad}$; and the time provided for the ramping of the phase coding gradients is designated with $T_{ramp}$. The total acquisition time is designated with $T_{acq}$ and the gradient strength in the radial scanning of k-space is designated with G. The image resolution $$R = FOV/N$$

follows from the extent of the field of view (FOV) and the matrix size N. The extent of k-space can be derived from this as $$K_{max} = \pm 1/(2\gamma R),$$

wherein $\gamma$ is the (as is known) the gyromagnetic ratio. Depending on the gradient strength G, the time $$T_{outer} = K_{max}/G$$

is required in order to code an outer point of k-space. For a selected echo time TE (time from the middle of the excitation pulse up to the beginning of the data acquisition, it follows that all points in the radius $$r = TE/(2T_{outer}) \cdot N$$

around the center of k-space cannot be measured in the radial portion of the magnetic resonance sequence, and consequently must be measured in a Cartesian manner, which means that the radius r describes the second region. The first region lies outside of the second region, starting from the center of k-space.

The number of measurement points to be scanned in a Cartesian manner can now be calculated as $$N_{Cart} = 4/3 \cdot \pi \cdot r^3.$$

Therefore, together with the number of radial spokes $N_{rad}$, overall a number of $N_{ges} = N_{Cart} + N_{rad}$ repetitions are measured in the total acquisition time $$T_{acq} = N_{ges} \cdot TR.$$

The repetition time is thereby limited by the radial portion of the measurement data acquisition. Add to the readout duration $T_{outer}$ that is required there the echo time TE; half the duration of the excitation pulse; and the time $T_{ramp}$ provided for ramping the phase coding gradients, wherein in the following—for the sake of simplicity—the time $T_{ramp}$ is defined such that it already includes the duration of the excitation pulse. The minimum possible repetition time consequently results as $$TR = T_{outer} + TE + T_{ramp}.$$

If these values are inserted into the formula of the total acquisition time $T_{acq}$, it follows that:

$$T_{acq} = (N_{rad} + 256/3 \cdot \pi \cdot (\gamma \cdot TE \cdot G \cdot FOV)^3) \cdot (TE + T_{ramp} + N/(2\gamma^* FOV^* G)).$$

A high-grade, non-linear curve is described with this. This curve can now be evaluated either [sic] in that the equation is solved analytically with regard to a minimum, in particular by calculating the derivative and calculation of the minimum of this, wherein it is also conceivable, however, that predetermined values for the gradient strength G are used in the formula for the total acquisition time $T_{acq}$, whereupon the value leading to the smallest total acquisition time $T_{acq}$ is selected.

The values for $T_{ramp}$ and TE are preferably for the most part predetermined, wherein $N_{rad}$, N and FOV are designed so as to be adjustable by a user.

In an example with FOV=300 mm, $T_{ramp}$=500 µs, $N_{rad}$=50000, TE=70 µs and N=256, a minimum measurement time results at a gradient strength of 9.2 mT/m.

it is now possible for this optimal value in the radial scanning of k-space in the second region to be selected and set automatically for the implementation of the magnetic resonance sequence, but it is also possible to specify the value for the gradient strength to a user as a recommendation. This user can then decide whether to follow the recommendation for the value of the gradient strength.

Furthermore, it is advantageous to provide a user interface via which a function for the recommendation of the gradient strength corresponding to the shortest total acquisition time can be activated and/or deactivated. The method to automatically determine an optimal gradient strength for the radial portion of the magnetic resonance sequence can consequently always be activated automatically, or can also be activatable or deactivatable by the user via an operating element in the user interface. The user can thus decide whether he or she will receive corresponding instructions.

Overall, the method according to the invention thus allows an automatic measurement time minimization by determining an optimal gradient strength for settings (the sequence parameters) predetermined by the user and/or by the system. An extremely user-friendly handling is thereby provided.

In addition to the method, the present invention also concerns a magnetic resonance device that has a control device designed to execute the method according to the invention. All statements with regard to the method according to the invention can analogously be transferred to the magnetic resonance device according to the invention, such that the advantages of the present invention can also be achieved with this device.

BRIEF DESCRIPTION OF THE DRAWINGS

FIG. 1 is a flowchart of an embodiment of the method according to the invention, FIG. 2 shows a curve of the total acquisition time depending on the gradient field strength.

FIG. 3 schematically illustrates a magnetic resonance device according to the invention.

DESCRIPTION OF THE PREFERRED EMBODIMENTS

FIG. 1 shows a flowchart of an exemplary embodiment of the method according to the invention. This embodiment involves preparation (optimized with regard to the total acquisition time) and execution of a PETRA magnetic resonance sequence in which a first region of k-space that corresponds to an imaging area located in a measurement volume of a magnetic resonance device is scanned by radial scanning of k-space along spokes that are defined starting from the center of k-space and proceed radially, while a second region including the center of k-space is scanned in a Cartesian manner by single point imaging. In its embodiment, the magnetic resonance sequence is parameterized by various sequence parameters in the acquisition of a defined imaging area, which sequence parameters are determined in Step 1 in that either they are already predetermined by the magnetic resonance device (presently with regard to the time provided for the ramping of the phase coding gradients and the echo time, which is chosen to be as short as possible) and/or are set by a user, presently with regard to the number of spokes to be scanned radially and the desired image resolution, consequently the size (extent) of the field of view and the matrix size. It is noted that, naturally, other sequence parameters—in particular also those that are not required for the following calculations—can be adjustable and/or predetermined by the magnetic resonance device.

In Step 2, an optimal gradient strength in the radial scanning in the first region is automatically determined for which the total acquisition time is minimal. For this, $$T_{acq} = (N_{rad} + 356/3 \ast \pi \ast (\gamma \ast TE \ast G \ast FOV)^3) \ast (TE + T_{ramp} + N/(2\gamma \ast FOV \ast G))$$

derived above is tested at a minimum of the total acquisition time $T_{acq}$ when it is understood as a correlation between the total acquisition time $T_{acq}$ and the gradient strength G.

FIG. 2 shows as an example the non-linear curve of the total acquisition time $T_{acq}$ depending on the gradient strength G for an example in which the extent of the field of view FOV=300 mm; the time $T_{ramp}$=500 µs is provided for the ramping of the phase coding gradients; the number of radial spokes to be acquired in the first region $N_{rad}$=50000; the echo time TE=70 µs; and the matrix size N=256 have been selected. In this example, the minimum measurement time is at 9.2 mT/m, as is apparent from FIG. 2.

In an optional Step 3, the optimal gradient strength for the radial acquisition that is determined automatically in Step 2 can be displayed as a suggestion to a user, whereupon this user either confirms or modifies the suggestion. However, it is also possible that the selection takes place completely automatically, and in the following the magnetic resonance sequence is then started automatically with the optimal gradient strength.

The image acquisition with the magnetic resonance sequence and the ideally set gradient strength for the radial scanning of k-space then takes place in Step 4.

It is further noted that an operating element with which this automatic determination of an optimal gradient strength can be deactivated and activated can be provided in the user interface of the magnetic resonance device.

Finally, FIG. 3 schematically shows a magnetic resonance apparatus 5 that—as is fundamentally known—has a magnet unit 6 into which a patient can be driven through a patient receptacle 7. A radio-frequency transmission/reception device (a body coil, for example) and the gradient coils can be provided (not shown in detail for clarity) encircling the patient receptacle 7.

The operation of the magnetic resonance apparatus 5 is controlled via a control device 8 which, in the image acquisition, can realize the PETRA magnetic resonance sequence with the set sequence parameters, in particular also the set, optimal gradient strength. The control device 8 is connected with an operating unit 9 which has a display device 10 and an input device 11. Adjustable sequence parameters can hereby be set. Predetermined sequence parameters can be stored in a storage device of the control device 8.

In particular, at the display device 10 a user interface 12 can be provided which the recommendation for the optimal gradient strength can possibly be output and in which and in which an operating element 13 can be provided in order to activate or deactivate the automatic calculation functionality of Step 2.

In each case, the control device 8 is designed to operate the magnetic resonance apparatus 5 to implement the method according to the invention.

Although modifications and changes may be suggested by those skilled in the art, it is the intention of the inventor to embody within the patent warranted hereon all changes and modifications as reasonably and properly come within the scope of his contribution to the art.

I claim as my invention:

1. A method to operate a magnetic resonance apparatus comprising:

acquiring magnetic resonance data by operating a magnetic resonance data acquisition unit according to data acquisition pulse sequence in which a radio-frequency excitation pulse, which excites nuclear spins in a subject, is radiated when a full strength of at least two activated phase coding gradients in said pulse sequence is reached;

entering magnetic resonance signals resulting from excitation of said nuclear spins into an electronic memory organized as k-space, by scanning k-space in a first region thereof that does not include a center of k-space, and scanning k-space in a Cartesian manner in a second region of k-space that remains without the first region;

providing sequence parameters for said data acquisition pulse sequence to a processor that describe a number of acquisitions of said first and second regions of k-space and a repetition time of said number of acquisitions;

in said processor, automatically determining, from said sequence parameters, a gradient field strength of said at least two phase coding gradients that corresponds to a shortest total acquisition time for executing said data acquisition pulse sequence; and making a designation of said gradient strength available at an output of said processor in an electronic form.

2. A method as claimed in claim 1 comprising operating said magnetic resonance data acquisition unit with a PETRA sequence, as said pulse sequence.

3. A method as claimed in claim 1 wherein scanning k-space in a Cartesian manner comprises implementing single point imaging in said second region of k-space.

4. A method as claimed in claim 1 comprising, at a display unit in communication with said processor, visually displaying a representation of said gradient field strength.

5. A method as claimed in claim 4 comprising, via a user interface in communication with said processor, allowing manual entry of a command that selectively activates or deactivates said display of said representation of said calculated gradient field strength.

6. A method as claimed in claim 1 comprising, from said processor, automatically controlling operation of said data acquisition unit according to said pulse sequence, with said calculated gradient field strength.

7. A method as claimed in claim 1 comprising selecting said sequence parameters from the group consisting of parameters describing an image resolution, parameters describing a size of a field of view, parameters describing a size of a matrix in k-space in which said data points are entered, parameters describing an echo time of said pulse sequence, parameters describing a number of radial spokes in said first region of k-space, and parameters describing a time within said pulse sequence for ramping said phase coding gradients.

8. A method as claimed in claim 1 comprising calculating said gradient field strength by calculating a minimum of:

$$T_{acq}=(N_{rad}+256/3*\pi*(\gamma*TE*G*FOV)^3)*(TE+T_{ramp}+N/(2\gamma*FOV*G))$$

for the total acquisition time, wherein $N_{rad}$ is the number of radial spokes to be acquired in k-space, TE is the echo time, G is the gradient strength, FOV is the size of the field of view, $T_{ramp}$ is the time provided for the ramping of the phase coding gradients, $\gamma$ is the gyromagnetic ratio of said nuclear spins, and N is the matrix size in k-space; or via use of predetermined values for the gradient strength in the formula for the total acquisition time and selection of the value leading to the lowest total acquisition time.

9. A magnetic resonance apparatus comprising:

a magnetic resonance data acquisition unit:

a control unit configured to operate the magnetic resonance data acquisition unit to acquire magnetic resonance data according to data acquisition pulse sequence in which a radio-frequency excitation pulse, which excites nuclear spins in a subject, is radiated when a full strength of at least two activated phase coding gradients in said pulse sequence is reached;

said control unit configured to enter magnetic resonance signals resulting from excitation of said nuclear spins into an electronic memory organized as k-space, by scanning k-space in a first region thereof that does not include a center of k-space, and scanning k-space in a Cartesian manner in a second region of k-space that remains without the first region;

a processor configured to receive sequence parameters for said data acquisition pulse sequence that describe a number of acquisitions of said first and second regions of k-space and a repetition time of said number of acquisitions;

said processor being configured to automatically determine, from said sequence parameters, a gradient field strength of said at least two phase coding gradients that corresponds to a shortest total acquisition time for executing said data acquisition pulse sequence; and said processor being configured to make a designation of said gradient strength available at an output of said processor in an electronic form.

10. A non-transitory, computer-readable data storage medium encoded with programming instructions, said data storage medium being loaded into a computerized control and evaluation system of a magnetic resonance apparatus, that also comprises a magnetic resonance data acquisition unit, said programming instructions causing said computerized control and evaluation system to:

operate the magnetic resonance data acquisition unit to acquire magnetic resonance data according to data acquisition pulse sequence in which a radio-frequency excitation pulse, which excites nuclear spins in a subject, is radiated when a full strength of at least two activated phase coding gradients in said pulse sequence is reached;

enter magnetic resonance signals resulting from excitation of said nuclear spins into an electronic memory organized as k-space, by scanning k-space in a first region thereof that does not include a center of k-space, and scanning k-space in a Cartesian manner in a second region of k-space that remains without the first region;

receive sequence parameters for said data acquisition pulse sequence that describe a number of acquisitions of said first and second regions of k-space and a repetition time of said number of acquisitions;

automatically determine, from said sequence parameters, a gradient field strength of said at least two phase coding gradients that corresponds to a shortest total acquisition time for executing said data acquisition pulse sequence; and make a designation of said gradient strength available at an output of said control and evaluation system in an electronic form.

* * * * *